United States Patent
Park et al.

(10) Patent No.: US 8,246,985 B2
(45) Date of Patent: Aug. 21, 2012

(54) PHARMACEUTICAL COMPOSITION COMPRISING LIPASE INHIBITOR AND LIPOPHILIC OIL ABSORBENT AND ORAL FORMULATION PREPARED THEREFROM

(75) Inventors: Jin Woo Park, Seoul (KR); Sung Ah Bin, Yongin-si (KR); Jeong A Lee, Yongin-si (KR); Jung Ju Kim, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 372 days.

(21) Appl. No.: 12/297,763

(22) PCT Filed: Apr. 20, 2007

(86) PCT No.: PCT/KR2007/001938
§ 371 (c)(1),
(2), (4) Date: Oct. 20, 2008

(87) PCT Pub. No.: WO2007/123338
PCT Pub. Date: Nov. 1, 2007

(65) Prior Publication Data
US 2009/0068277 A1    Mar. 12, 2009

(30) Foreign Application Priority Data

Apr. 20, 2006    (KR) .......................... 10-2006-0035687

(51) Int. Cl.
*A61K 9/48*    (2006.01)
*A61K 9/52*    (2006.01)
*A61K 9/20*    (2006.01)

(52) U.S. Cl. ......... 424/451; 424/452; 424/457; 424/465

(58) Field of Classification Search .......................... None
See application file for complete search history.

(56) References Cited

U.S. PATENT DOCUMENTS

| | | | |
|---|---|---|---|
| 6,251,421 B1 | 6/2001 | Niazi | |
| 6,468,559 B1 * | 10/2002 | Chen et al. | 424/451 |
| 6,641,808 B1 * | 11/2003 | Bojrab | 424/93.3 |
| 6,734,314 B2 | 5/2004 | Keri et al. | |
| 2003/0091624 A1 * | 5/2003 | Szymczak et al. | 424/465 |
| 2003/0181512 A1 * | 9/2003 | de Smidt et al. | 514/449 |
| 2005/0100535 A1 * | 5/2005 | Farmer et al. | 424/93.46 |

FOREIGN PATENT DOCUMENTS

| | | |
|---|---|---|
| CA | 2507971 A1 | 7/2004 |
| CA | 2617140 A1 | 2/2007 |
| CA | 2383036 A1 | 3/2011 |
| CN | 1373656 A | 10/2002 |
| CN | 1373659 A | 10/2002 |
| WO | 0009123 A1 | 2/2000 |
| WO | 01/19340 A1 | 3/2001 |
| WO | 01/19378 A2 | 3/2001 |
| WO | 03090742 A1 | 11/2003 |
| WO | WO 03/090742 * | 11/2003 |
| WO | 2004/060401 A1 | 7/2004 |

OTHER PUBLICATIONS

Office Action from related Canadian Application No. 2,647,893, issued on Jan. 25, 2012, 2 pages.

* cited by examiner

*Primary Examiner* — Brian Gulledge
(74) *Attorney, Agent, or Firm* — Rothwell, Figg, Ernst & Manbeck, P.C.

(57) ABSTRACT

This invention provides a pharmaceutical composition comprising a lipase inhibitor; a lipophilic oil absorbent selected from the group consisting of hydrogenated castor oil, hydrogenated vegetable oil, glyceryl behenate, glyceryl palmitostearate and a mixture thereof; and a pharmaceutically acceptable additive, an oral formulation of a lipase inhibitor prepared there from and a method for preparing said formulation. The formulation of the present invention can minimize side effects such as oily spotting, fatty/oily stool, abdominal distension and flatus, and thus it can be advantageously used for preventing or treating obesity and hyperlipaemia.

19 Claims, No Drawings

PHARMACEUTICAL COMPOSITION COMPRISING LIPASE INHIBITOR AND LIPOPHILIC OIL ABSORBENT AND ORAL FORMULATION PREPARED THEREFROM

CROSS REFERENCE TO RELATED APPLICATIONS

This application is a 35 USC §371 National Phase Entry Application from PCT/KR2007/001938, filed Apr. 20, 2007, and designating the United States. This application claims priority under 35 U.S.C. §119 based on Korean Patent Application No. 10-2006-0035687 filed Apr. 20, 2006, which is incorporated herein in its entirety.

FIELD OF THE INVENTION

The present invention relates to a pharmaceutical composition comprising a lipase inhibitor and a lipophilic oil absorbent, an oral formulation prepared therefrom, and a method for preparing same.

BACKGROUND OF THE INVENTION

Lipase inhibitors have been used in the prevention or treatment of obesity and hyperlipaemia by inhibiting the activity of lipase which hydrolyzes triglyceride to form glycerol and free fatty acid, thereby reducing fat absorption into the body. Such lipase inhibitors include lipstatin, orlistat, panclicins, hesperidin, ebelactones, esterastin and derivatives thereof, and valilactone, among these, orlistat known as tetrahydrolipstatin is derived from natural substance excreted by *Streptomyces toxytricini*. Orlistat is a strong inhibitor of various lipase including gastric lipase, pancreatic lipase and carboxyl ester lipase, and its use for the control or prevention of obesity and hyperlipidaemia is described in U.S. Pat. No. 4,598,089, and it is sold under the trademark XENICAL® to be administered in 120 mg dose per meal to inhibit fat uptake by about 30%.

The unabsorbed fat by the action of the lipase inhibitor, however, reduces water absorption in the colon, and it forms a separated oil component in the stool, inducing such side effects as oily spotting, abdominal distension, flatus, fecal urgency, fatty/oily stool, increased defecation and fecal incontinence which lead to patients' difficulties and incompliance on lipase inhibitor dosage (See Mark Fox et al., *Diseases of the Colon & Rectum*, 47, 2147-2156, 2004). Accordingly, many attempts have been made to reduce such side effects.

Oily spotting, in particular, has been occasionally observed in the stool of patients treated with lipase inhibitors, and many studies have been conducted to solve such side effects through the use of surfactants, emulsifiers or dispersants for dispersing unabsorbed fat in the colon, or through the use of high-viscous substances such as dietary fiber for increasing the viscosity of water in the colon, which is effective in the prevention of oil emulsion coalescence. Also, the physical adsorption of oil with a lipophilic compound has been studied.

For example, International Patent Publication WO 2000/09122 discloses that the oil emulsion coalescence can be minimized when an emulsifier such as Ryoto Sugar Ester is used in mixing or dispersing water and oil and combining the resulting mixture with a hydrophilic hydro colloidal thickener. However, such an emulsifier addition can increase fat absorption in the upper colon, and the thickener is not sufficiently effective in adsorbing free oil.

International Patent Publication WO 2001/19340 discloses that the oil leakage phenomenon can be reduced by solubilizing orlistat with a surfactant and at least one dispersant, to improve lipase inhibition and free oil dispersion. However, the solubilized orlistat tends to be absorbed into the blood through the gastrointestinal (GI) tract, which may induce unexpected adverse effects.

International Patent Publication WO 2002/98412 discloses that the side effects of unabsorbed fat can be reduced by using sucrose fatty acid ester surfactant to increase the orlistat activity in the GI and to convert free oil into a stable emulsion in the colon. However, the formation of a stable emulsion in the GI tract by the addition of a surfactant is difficult to achieve because of the unsteady environment of the GI tract, also it requires an appropriate pharmaceutical mean for the surfactant to function as an enhancer of orlistat in the small GI as well as an emulsifier in the colon.

Furthermore, International Patent Publication WO 2003/090742 discloses that the oil emulsion coalescence can be prevented by using konjac (glucomannan) together with a lipase inhibitor to increase water viscosity in the colon and stabilize unabsorbed oil. This is, however, possible only in vitro experiment conditions having a limited moisture content, but not in the colon which undergoes frequent water absorption.

Also, International Patent Application WO 2000/09123 discloses the reduction of oil leakage by the use of chatoyant for adsorbing free fat, but it is reported that such an effect can not be achieved in a clinical experiment (See M. D. Gades and J. S. Stern, *International Journal of Obesity*, 26, 119-122, 2002; and Roberto Guerciolini et al., *Obesity Research*, 9(6): 364-367, 2001).

Accordingly, the present inventors have endeavored to reduce side effects caused by a lipase inhibitor and found that a lipophilic oil absorbent having a low density in the solid state can adsorb unabsorbed oil and increase the viscosity thereof, thereby minimizing the side effects.

SUMMARY OF THE INVENTION

It is an object of the present invention to provide a pharmaceutical composition comprising a lipase inhibitor which can minimize side effects caused by the uptake of a lipase inhibitor.

It is another object of the present invention to provide an oral formulation prepared from said pharmaceutical composition and a method for preparing same.

In accordance with one aspect of the present invention, there is provided a pharmaceutical composition comprising 1) a lipase inhibitor; 2) a lipophilic oil absorbent selected from the group consisting of hydrogenated castor oil, hydrogenated vegetable oil, glyceryl behenate, glyceryl palmitostearate and a mixture thereof; and 3) a pharmaceutically acceptable additive.

In accordance with another aspect of the present invention, there is provided a method for preparing an oral formulation of a lipase inhibitor, which comprises 1) mixing a lipase inhibitor and a pharmaceutically acceptable additive to obtain a mixture, and optionally granulating the resulting mixture to obtain granules;

2) mixing a lipophilic oil absorbent selected from the group consisting of hydrogenated castor oil, hydrogenated vegetable oil, glyceryl behenate, glyceryl palmitostearate and a mixture thereof, and a pharmaceutically acceptable additive, and granulating the resulting mixture to obtain granules;

3) coating the granules obtained in 2) with an enteric coating agent; and 4) formulating the coated granules obtained in 3) and the mixture or granules obtained in 1), separately, and mixing the resulting formulations; or mixing the coated granules obtained in 3) and the mixture or granules obtained in 1), followed by formulating the resulting mixture.

In accordance with still another aspect of the present invention, there is provided an oral formulation of a lipase inhibitor prepared by said method.

DETAILED DESCRIPTION OF THE INVENTION

The inventive composition of a lipase inhibitor is characterized by comprising a lipophilic oil absorbent having a low density in the solid state to adsorb free oil and increase the viscosity thereof, thereby overcoming various side effects caused by free oil.

The lipase inhibitor used as an effective ingredient in the inventive composition is any compound that is capable of inhibiting the activity of a lipase such as a gastric lipase and pancreatic lipase, and representative examples of the lipase inhibitor include lipstatin, orlistat, panclicins, hesperidin, ebelactones, esterastin and derivatives thereof, valilactone and a pharmaceutically acceptable salt thereof.

The lipophilic oil absorbent should have a melting point higher than the body temperature so that it exists as a solid, and a density lower than that of water so that it can be easily dispersed in an oil layer and brought into contact with oil. The lipophilic oil absorbent dispersed in the oil layer increases the viscosity of liquid oil or adsorb liquid oil depending on the relative amounts thereof, thereby converting the liquid oil into a semisolid or solid fat. Such a physical change of oil reduces the fluidity of oil generated by the lipase inhibitor to minimize the leakage of free oil.

Examples of the lipophilic oil absorbent which is preferably used in the inventive composition include hydrogenated castor oil, hydrogenated vegetable oil, glyceryl behenate, glyceryl palmitostearate and a mixture thereof, among which hydrogenated castor oil and hydrogenated vegetable oil are more preferred.

Preferred example of the hydrogenated vegetable oil is type I hydrogenated vegetable oils, among which hydrogenated cottonseed oil, hydrogenated palm oil and hydrogenated soybean oil are more preferred.

The inventive pharmaceutical composition comprises the lipophilic oil absorbent in an amount ranging from 10 to 5,000 parts by weight, preferably from 400 to 5,000 parts by weight, based on 100 parts by weight of the lipase inhibitor.

The inventive pharmaceutical composition may further comprise a hydrophilic hydrogel and/or anti-flatulent agent.

The hydrophilic hydrogel is a water-soluble or water-absorbable polymer which increases the viscosity of water or absorbs excessive water in the colon, and thus it retains moisture in its structure to increase the viscosity of the stool in the colon and reduce the volume thereof.

In principle, the unabsorbed oil generated by the uptake of a lipase inhibitor is decomposed by microbials in the colon to produce fatty acid, and the fatty acid prevents water absorption to increase the volume of the stool, reduce the viscosity thereof and modify the composition thereof, while the oil emulsion coalescence in the solid stool leads to such side effects as oil leakage, fecal urgency and diarrhea (See R. C. Spiller et al., *Gastroenterology,* 91, 100-107, 1986; Helmut V. et al., *Gastroenterology,* 65, 744-749, 1973; Wayne L. Ambroze et al., *Diseases of the Colon & Rectum,* 34(1), 1-7, 1991; Mark Fox et al., *Diseases of the Colon & Rectum,* 47(12), 2147-2156, 2004; and M. Fox et al., *Aliment. Pharmacol. Ther.,* 19, 311-321, 2004). Accordingly, the hydrophilic hydrogel which is used together with the lipophilic oil absorbent can absorb excessive water in the colon while increasing the viscosity of water, to reduce the side effects.

Examples of the hydrophilic hydrogel include polyethylene oxide, hydroxyalkyl cellulose, hydroxypropylalkyl cellulose, polyvinylalcohol, polyvinylpyrrolidone, sodium carboxymethyl cellulose, carbopol, sodium alginate, xanthan gum, locust bean gum, cellulose gum, gellan gum, tragacanth gum, karaya gum, guar gum, acacia gum, psyllium and a mixture thereof.

Preferred examples of the polyethylene oxide include, but are non-limited to, those having a molecular weight ranging from 1,000 to 7,000 kDa. Preferred examples of hydroxyalkyl cellulose include, but are non-limited to, hydroxyethyl cellulose and hydroxypropyl cellulose. Preferred hydroxypropylalkyl cellulose is, but is non-limited to, hydroxypropylmethyl cellulose.

The inventive pharmaceutical composition comprises the hydrophilic hydrogel in an amount ranging from 10 to 1,000 parts by weight, based on 100 parts by weight of the lipase inhibitor.

Also, the anti-flatulent agent prevents abdominal distension, gas discharge and free oil leakage which are occasionally observed on the uptake of a lipase inhibitor. Examples of the anti-flatulent agent include active carbon, simeticone and derivatives thereof, cisapride, neostigmine and derivatives thereof, a muscle relaxant, peppermint oil and a mixture thereof, among which simeticone is preferred.

The inventive pharmaceutical composition comprises the anti-flatulent agent in an amount ranging from 20 to 2,000 parts by weight, based on 100 parts by weight of the lipase inhibitor.

Also, the inventive pharmaceutical composition may further comprise at least one pharmaceutically acceptable additive, e.g., binders, diluents, swelling agents, surfactants, lubricants, antioxidants, effervescent agents, flavors.

Examples of the binder include, but are non-limited to, polyvinylpyrrolidone, kopovidone, gelatin, starch, sucrose, methyl cellulose, ethyl cellulose, hydroxyethyl cellulose, hydroxypropyl cellulose, hydroxypropyl alkyl cellulose and a mixture thereof.

Examples of the diluent include, but are non-limited to, lactose, dextrin, mannitol, sorbitol, starch, microcrystalline cellulose, calcium hydrogen phosphate, anhydrous calcium hydrogen phosphate, calcium carbonate, sugars and a mixture thereof.

Examples of the swelling agent include, but are non-limited to, cross-linked polyvinylpyrrolidone, cross-linked sodium carboxymethyl cellulose, cross-linked calcium carboxymethyl cellulose, cross-linked carboxymethyl cellulose, sodium starch glycolate, carboxymethyl starch, sodium carboxymethyl starch, potassium methacrylate-divinylbenzene copolymer, amylose, cross-linked amylose, starch derivatives, microcrystalline cellulose and cellulose derivatives, cyclodextrin and dextrin derivatives, and a mixture thereof.

Examples of the surfactant include, but are non-limited to, anionic surfactants, non-ionic surfactants, zwitterionic surfactants and a mixture thereof. Preferably, the surfactants is selected from the group consisting of poly(oxyethylene) sorbitan fatty acid ester, poly(oxyethylene) stearate, poly(oxyethylene) alkyl ether, polyglycolated glyceride, poly(oxyethylene) caster oil, sorbitan fatty acid ester, poloxamer, fatty acid salt, bile salt, alkyl sulfate, lecithin, mixed micelle of bile salt and lecithin, glucose ester vitamin E TPGS (D-α-tocopheryl polyethylene glycol 1000 succinate), sodium lauryl sulfate and a mixture thereof.

Examples of the lubricant include, but are non-limited to, stearic acid, stearic acid salt, talc, corn starch, carnauba wax, light anhydrous silicic acid, magnesium silicate, synthetic aluminum silicate, hardened oil, white beeswax, titanium oxide, microcrystalline cellulose, Macrogol 4000 and 6000, isopropyl myristate and calcium hydrogen phosphate.

The pharmaceutically acceptable additive may be contained in an amount ranging from 1 to 5,000 parts by weight, based on 100 parts by weight of the lipase inhibitor in the inventive pharmaceutical composition.

Furthermore, the present invention provides a method for preparing an oral formulation of a lipase inhibitor, which comprises 1) mixing a lipase inhibitor and a pharmaceutically acceptable additive to obtain a mixture, and optionally granulating the resulting mixture to obtain granules;

2) mixing a lipophilic oil absorbent selected from the group consisting of hydrogenated castor oil, hydrogenated vegetable oil, glyceryl behenate, glyceryl palmitostearate and a mixture thereof, and a pharmaceutically acceptable additive, and granulating the resulting mixture to obtain granules;

3) coating the granules obtained in 2) with an enteric coating agent; and 4) formulating the coated granules obtained in 3) and the mixture or granules obtained in 1), separately, and mixing the resulting formulations; or mixing the coated granules obtained in 3) and the mixture or granules obtained in 1), followed by formulating the resulting mixture.

The inventive method is characterized in that the lipophilic oil absorbent-containing granules are prepared separately from the lipase inhibitor so that the lipophilic oil absorbent is brought into contact with free oil after the activation of the lipase inhibitor, and the granules are coated with an enteric coating agent or a coating agent soluble in the colon to minimize both the amount of the lipophilic oil absorbent administered and the influence thereon by the diet while preventing the lipophilic oil absorbent from the decomposition or absorption by digestive enzymes.

More specifically, each of the lipase inhibitor and the lipophilic oil absorbent is mixed with a pharmaceutically acceptable additive to prepare a mixture or granules. The lipophilic oil absorbent is preferably in the form of granules for coating. The granules may be, but are non-limited to, in the form dried, wet, melted or fluidized granules prepared by such processes as high speed rotation, direct compression, molding or extrusion.

In the preparation of each of the lipase inhibitor- and the lipophilic oil absorbent-containing granules or mixture, a hydrophilic hydrogel may be added so that it can absorb water unabsorbed in the colon or increase the viscosity thereof, and/or an anti-flatulent agent may be added to reduce abdominal distension caused by excessive gas generation due to abnormal digestion.

The lipophilic oil absorbent-containing granules are preferably coated with an enteric coating agent or a coating agent soluble in the colon. The resulting coating layer allows the lipophilic oil absorbent to affect only the unabsorbed free oil generated by the action of the lipase inhibitor in the lower small intestine, and enhances the stability, release control, initial burst release prevention and taste masking of a drug.

The coating layer may be formed by dissolving at least one enteric coating agent in a solvent to obtain a coating solution and coating the granules with the solution via spraying/jetting using a pan coater or fluidized bed device, electrostatic powder coating, drying, hot-melt coating process or a combination thereof.

Examples of the coating agent which may be used in such a coating process include ethyl cellulose, shellac, ammonio methacrylate copolymer, aminoalkyl methacrylate copolymer, methacrylic acid copolymer, polyvinylacetate, polyvinylpyrrolidone, polyvinylalcohol, hydroxymethyl cellulose, hydroxyethyl cellulose, hydroxypropyl cellulose, hydroxybutyl cellulose, hydroxypentyl cellulose, hydroxypropyl methyl cellulose, hydroxypropyl butyl cellulose, hydroxypropyl pentyl cellulose, hydroxyalkyl cellulose phthalate, sodium cellulose acetate phthalate, cellulose acetyl phthalate, cellulose ether phthalate, an anionic copolymer of methacylic acid and methyl or ethyl methacrylate, hydroxypropyl methyl cellulose phthalate, hydroxypropyl methyl cellulose acetate succinate, cellulose acetyl phthalate, Opadry® (Colorcon Co.), and a mixture thereof.

The coating agent is preferably used in an amount of 1 to 50 wt % based on the weight of the granules for coating.

Also, the solvent used for preparing the coating solution includes water, ethanol and other alcohols (methanol, isopropyl alcohol), acetone, acetonitrile, methylene chloride, ether, hexane, chloroform, 1,4-dioxane, tetrahydrofuran, dimethyl sulfoxide, ethyl acetate, methyl acetate and a mixture thereof.

The coating layer may further comprise plasticizers, as well as colorants, antioxidants, talc, titanium dioxide or flavors. Examples of the plasticizer include castor oil, fatty acids, substituted triglyceride, glyceride, triethyl citrate, polyethylene glycol having a molecular weight of 300 to 50,000 Da and their derivatives, and a mixture thereof.

The lipase inhibitor-containing mixture or granules and the lipophilic oil absorbent-containing granules before or after coating may be individually formulated prior to mixing, or they may be mixed and then formulated. The formulation may take various oral administration forms such as a tablet, chewable tablet, coated tablet, pill, powder, capsule, sachet, syrup, emulsion, microemulsion, suspension and the like. Such an oral formulation may contain pharmaceutically acceptable carriers and excipients such as cellulose, calcium silicate, corn starch, lactose, sucrose, dextrose, calcium phosphate, stearic acid or its magnesium or calcium salt, gelatin, talc, surfactant, suspension, emulsifier or diluent.

For the inventive oral formulation of a lipase inhibitor, the administered amount is determined depending on a typical daily dose of the lipase inhibitor, e.g., 60 to 720 mg for orlistat, which may be properly adjusted according to various relevant factors including the condition to be treated, the severity of the patient's symptoms, the administration frequency and the physician's decision, and also it may be administered in a single dose or in divided doses.

The lipase inhibitor formulation comprising the lipophilic oil absorbent of the present invention can minimize such side effects as abdominal distension, oily spotting, fatty/oily stool, fecal urgency, increased defecation and fecal/free oil incontinence caused by the uptake of the lipase inhibitor and enhance patient's compliance, and thus it can be efficiently used for preventing or treating obesity and hyperlipaemia.

The present invention is further described and illustrated in Examples provided below, which are, however, not intended to limit the scope of the present invention.

EXAMPLE

Test Example 1

Selection of Lipophilic Oil Absorbent

In order to select a lipophilic oil absorbent that is capable of adsorbing unabsorbed free oil by the action of a lipase inhibitor, various substances known as a dispersant or adsorbent were subjected to an adsorption test as follows. 1.5 g of each ingredient listed in Table 1 (excepted for 0.1 g of each of hydroxypropyl methyl cellulose and polyethylene oxide, 0.5 g of light anhydrous silicic acid), 5 g of soybean oil and 15 g of purified water were mixed in a test tube for 2 minutes and centrifuged at 3,000 g for 5 minutes. After separating the supernatant oil layer, the oil adsorption degree of each substance was determined.

TABLE 1

| | Substance | Amount of remained oil (g) | Adsorption (%) |
|---|---|---|---|
| Dispersant | Polyvinylpyrrolidone (BASF) | 4.14 | 17.27 |
| | Hydroxypropyl methyl cellulose (4,000 cp, Dow chemical company) | 3.41 | 31.80 |
| | Polyethylene oxide (Mw 7,000,000, Dow chemical company) | 4.05 | 19.07 |
| | Poloxamer (Poloxamer 407, BASF) | 0.56 | 80.80 |
| | Polyethylene glycol (Mw 6,000, Sigma-Aldrich) | 4.28 | 85.67 |
| | Polyoxyethylene(2) cetyl ether (Brij 52, Sigma-Aldrich) | 2.79 | 2.79 |
| | Polyoxyethylene(100) stearyl ether (Brij 700, Sigma-Aldrich) | 0.76 | 5.07 |
| | Labrafil (Labrafil M 2130 CS, Gattefosse) | 3.00 | 60.07 |
| | Gelucire (Gelucire 44/14, Gattefosse) | 1.05 | 21.00 |
| | Polyoxyl 35 castor oil (Cremophor EL, Gattefosse) | 0.14 | 1.80 |
| | Polysorbate (Tween 80, Shiyo pure chemicals Co., LTD) | 0.00 | 100.00 |
| | Sorbitan trioleate (Span 85, Shiyo pure chemicals Co., LTD) | 0.17 | 1.13 |
| | Sucrose ester (scro ester 15, Gattefosse) | 0.00 | 100.00 |
| | Sodium lauryl sulfate | 0.00 | 100.00 |
| Adsorbent | Cross-linked sodium carboxymethyl cellulose | 4.65 | 6.9 |
| | Hydroxypropy cellulose (L-type, Shinetsu) | 4.35 | 12.9 |
| | Cross-linked polyvinylpyrrolidone (BASF) | 3.94 | 21.3 |
| | Hydrogenated castor oil (Corechemicals) | 1.96 | 60.8 |
| | Chitosan (Sigma-Aldrich) | 3.77 | 24.6 |
| | Glyceryl behenate (Gattefosse) | 1.98 | 60.4 |
| | Glyceryl palmitostearate (Gattefosse) | 0.65 | 87.0 |
| | Microcrystalline cellulose | 3.98 | 20.4 |
| | Light anhydrous silicic acid (Aerosil) | 1.13 | 77.4 |
| | Eudragit (Eudragit E PO, Degussa) | 2.53 | 49.4 |
| | Eudragit (Eudragit RL PO, Degussa) | 3.91 | 21.8 |
| | Eudragit (Eudragit RS, Degussa) | 4.13 | 17.4 |
| | Ethyl cellulose (Hercules) | 3.09 | 38.2 |
| | Carnauba was | 3.38 | 32.4 |
| | Sodium alginate (ISP technologies, INC.) | 2.35 | 47.0 |

In table 1, the amount of oil remained was measured from the weight of the oil layer after adsorption, and the adsorption (%) means the ratio of the amount of oil adsorbed (which is obtained by subtracting the remained oil amount from the total oil amount) to the total amount of oil. On using a dispersant, the amount of oil remained means the oil amount of a supernatant excepting oil dispersed layer, and the adsorption (%) means the ratio of the oil amount within the dispersing layer to the total oil amount (5 g).

Accordingly, the poloxamer and polyethylene glycol samples separated into oil, oil-dispersed and water layers showed an adsorption of 80% or higher, this means that the oil layer contains oil in an amount of 20% or less of the initial oil amount. However, the oil-dispersed layer has still a low viscosity, and represents characteristics similar to the oil layer, except for density, which is not substantially effective for reducing free oil leakage.

For the dispersant, the adsorption of 100% represents that oil is present in the only oil-dispersed layer on a water layer, and thus, it is impossible to separate the only oil or water phase. Also, the oil-dispersed layer has still a low viscosity, so free oil leakage may be not reduced.

Accordingly, sucrose ester, sodium lauryl sulfate, polysorbate representing 100% adsorption has good dispersion which may however, be unstable in the colon having insufficient moisture and increase the emulsion of dietary fat and the oil absorption.

Meanwhile, the adsorbents adsorb oil in a solid or semisolid state, which exists separately from oil or water phase. Particularly, hydrogenated castor oil, glyceryl behenate, glyceryl palmitostearate and light anhydrous silicic acid have good adsorption, even after centrifugation, to form the semisolid phase of oil. Among these, light anhydrous silicic acid adsorbs both of water and oil and has low density, which is not suitable for using in quantification or as an additive. For glyceryl behenate and glyceryl palmitostearate, some oil leakage was observed from the semi-solid phase of oil. Particularly, glyceryl palmitostearate is preferred in terms of its high adsorption, although having a relatively low melting point to become hard powders which require a separate milling process.

Also, hydrogenated castor oil is most preferred since it maintains stable oil adsorption at 37° C. as well as room temperature.

Example 1

Preparation of Orlistat-Containing Granules

Orlistat, microcrystalline cellulose, sodium starch glycolate and sodium lauryl sulfate were filtered through No. 30 mesh in an amount listed in Table 2 and mixed. Thereto, a solution of polyvinylpyrrolidone K30 in ethanol was added, and the resulting mixture was filtered through No. 14 mesh prior to drying and was filtered through No. 16 mesh to form granules, to which talc was added.

TABLE 2

| Ingredient | Amount (mg) |
| --- | --- |
| Orlistat | 120.00 |
| Microcrystalline cellulose | 93.60 |
| Sodium starch glycolate | 7.20 |
| Polyvinylpyrrolidone K30 | 12.00 |
| Anhydrous ethanol | 108.00* |
| Sodium lauryl sulfate | 7.20 |
| Talc | 0.24 |
| Total | 240.24 |

*removed during drying

Examples 2 to 11

Preparation of Hydrogenated Castor Oil-Containing Granules

Ingredients listed in Table 3 were filtered through No. 30 mesh and mixed, and the resulting mixture was granulated by spraying purified water in a fluidized bed device at a high rotation rate, to obtain granules containing hydrogenated castor oil.

TABLE 3

| Ingredient | Ex. 2 | Ex. 3 | Ex. 4 | Ex. 5 | Ex. 6 | Ex. 7 | Ex. 8 | Ex. 9 | Ex. 10 | Ex. 11 |
| --- | --- | --- | --- | --- | --- | --- | --- | --- | --- | --- |
| Hydrogenated castor oil (g) | 350 | 180 | 180 | 250 | 250 | 250 | 200 | 200 | 400 | 405 |
| Microcrystalline cellulose (g) | 350 | 120 | 120 | — | — | — | — | 40 | 50 | 45 |
| Hydroxypropyl methyl cellulose (L-type) (g) | — | 40 | 40 | 50 | — | 50 | 40 | 40 | 50 | — |
| Lactose (g) | — | — | 60 | 200 | 200 | 200 | 80 | 80 | — | — |
| Polyvinylpyrrolidone (K30) (g) | — | — | — | 60 | — | — | — | — | — | — |
| Calcium hydrogen phosphate (g) | — | 60 | — | — | — | — | — | — | — | — |
| Cross-linked sodium carboxymethyl cellulose (g) | 70 | — | — | — | 50 | 50 | 40 | 40 | — | — |

Examples 12 and 13

Coating of Hydrogenated Castor Oil-Containing Granules

The granules prepared in Examples 9 and 11 were selected for a size of 20 to 45 mesh, and the selected granules were placed in a Wurster fluidized bed equipment and coated by spraying a coating solution prepared from the ingredients listed in Table 4 at a temperature of 29 to 31° C.

TABLE 4

| Ingredient | Ex. 12 | Ex. 13 |
| --- | --- | --- |
| Granules used | Granules of Ex. 9, 800 g | Granules of Ex. 11, 700 g |
| Eudragit FS 30D | 516.13 g | — |
| Eudragit L30D55 | — | 463.75 g |
| Talc | 77.41 g | 70 g |
| Triethyl citrate | 7.742 g | 14 g |
| Purified water | 442.17 g | 327.25 g |

Thus, the enteric coating of hydrogenated castor oil granulated separately from the lipase inhibitor allows the activation of hydrogenated castor oil in the only small intestine or colon, and it can minimize the affect of fat contained in the diet and digestive enzymes such as lipase as well as the lipase inhibitor thereon.

Examples 14 to 20

Preparation of Mixed Formulation

The orlistat-containing granules prepared in Example 1 were mixed with the granules prepared in Example 13 and other additives according to an amount listed in Table 5. Each mixture of Examples 14, 15, 19 and 20 was filled in a sachet, respectively, and each mixture of Examples 16 to 18 was compressed to obtain a tablet, respectively.

TABLE 5

|  | Ex. 14 | Ex. 15 | Ex. 16 | Ex. 17 | Ex. 18 | Ex. 19 | Ex. 20 |
| --- | --- | --- | --- | --- | --- | --- | --- |
| Granules of Ex. 1 (mg) | 240.24 | 240.24 | 240.24 | 240.24 | 240.24 | 240.24 | 240.24 |
| Granules of Ex. 13 (mg) | 5 | 3 | 1 | 1 | 1 | — | — |
| Polyethylene oxide (Dow chemical company) (mg) | — | 200 | 200 | 200 | — | 200 | — |
| Psyllium (mg) | — | — | — | — | 200 | — | 200 |
| Simeticon (mg) | — | — | 60 | — | — | — | — |
| Total weight (g) | 5.24 | 3.44 | 1.50 | 1.44 | 1.44 | 0.44 | 0.44 |

Test Example 2

In Vivo Experiment

The formulations prepared above were evaluated for the reduction of side effects. Specifically, each of formulations and olive oil were administered to rabbits, from which cecal extract was obtained and the amount of free oil therein was quantified. The cecum stores temporally fat which is not absorbed by orlistat, and some of unabsorbed liquid oil was bound in a solid phase and the other exists as suspended oil.

The administration was conducted using rabbits (2-2.5 kg), the control group administered with only olive oil, and the comparative group administered orlistat granules (XENICAL®) and olive oil. Each group of rabbits was administered with the formulation as shown in Table 6 in three times per a day (8 times interval) with allowing free diet between each interval. After 5 hours, rabbits were sacrificed and their cecal contents were diluted with purified water and the supernatant was extracted. The extract was centrifuged (at 2000 g for 30 min.) to separate an oil layer and measure the amount of free oil. The results are shown in Table 6.

In Table 6, the amount of free oil means that contained in 1 g of cecal contents.

formulation of Example 15, compared to that in the comparative group since the formulation of Example 15 further contains hydrophilic hydrogel which can absorb and control even unabsorbed water. The formulations of Examples 19 and 20, which contain a lipase inhibitor and a hydrophilic hydrogel in the absence of lipophilic oil absorbent, showed slightly improved effect on the reduction of free oil, compared with the comparative group.

Meanwhile, the oil remained in the cecum may be removed itself or together with the stool since the stool and moisture are coexisted in the cecum and the moisture is absorbed in the colon.

Thus, the coated granules comprising hydrogenated castor oil as a lipophilic oil absorbent can adsorb unabsorbed oil after the activation of orlistat or increase the viscosity thereof to minimize such side effects as oily spotting. Also, the addition of hydrophilic hydrogel to the coated granules can improve the absorption of unabsorbed water to reduce the oil leakage from the stool and the generation of further free oil.

While the invention has been described with respect to the above specific embodiments, it should be recognized that various modifications and changes may be made and also fall within the scope of the invention as defined by the claims that follow.

What is claimed is:

1. A pharmaceutical composition comprising a) a lipase inhibitor; b) a lipophilic oil absorbent hydrogenated castor oil; and c) a pharmaceutically acceptable additive, wherein said lipophilic oil absorbent hydrogenated castor oil is enterically-coated to keep said lipophilic oil absorbent hydrogenated castor oil separate from said lipase inhibitor.

TABLE 6

|  | Control | Comparative | Ex. 14 | Ex. 15 | Ex. 19 | Ex. 20 |
| --- | --- | --- | --- | --- | --- | --- |
| Rabbit numbers (N) | 6 | 6 | 3 | 3 | 3 | 3 |
| Single dose (g) of formulation per rabbit | 0 | 0.24 | 5.24 | 3.44 | 0.44 | 0.44 |
| Single dose (g) of olive oil per rabbit | 20 | 20 | 20 | 20 | 20 | 20 |
| Amount of free oil (g), (Aver. ± S. D.) | 0.032 ± 0.026 | 0.156 ± 0.064 | 0.060 ± 0.025 | 0.043 ± 0.042 | 0.147 ± 0.026 | 0.099 ± 0.022 |

As shown in Table 6, the amount of free oil in the comparative group was about 5 times more compared to that of the control group, while it became reduced by 60% in the application of the formulation of Example 14 due to the adsorption capacity of hydrogenated castor oil. Besides, the amount of free oil became reduced by 70% in the application of the 2. The pharmaceutical composition of claim 1, wherein the lipase inhibitor is selected from the group consisting of lipstatin, orlistat, panclicins, hesperidin, ebelactones, esterastin and derivatives thereof, valilactone and a pharmaceutically acceptable salt thereof.

3. The pharmaceutical composition of claim 1, wherein the amount of the lipophilic oil absorbent hydrogenated castor oil is in the range of 10 to 5,000 parts by weight, based on 100 parts by weight of the lipase inhibitor.

4. The pharmaceutical composition of claim 1, which further comprises an anti-flatulent agent, hydrophilic hydrogel or a mixture thereof.

5. The pharmaceutical composition of claim 4, wherein the anti-flatulent agent is selected from the group consisting of active carbon, simeticone and derivatives thereof, cisapride, neostigmine and derivatives thereof, a muscle relaxant, peppermint oil and a mixture thereof.

6. The pharmaceutical composition of claim 4, wherein the amount of the anti-flatulent agent is in the range of 20 to 2,000 parts by weight, based on 100 parts by weight of the lipase inhibitor.

7. The pharmaceutical composition of claim 4, wherein the hydrophilic hydrogel is selected from the group consisting of polyethylene oxide, hydroxyalkyl cellulose, hydroxypropyl alkyl cellulose, polyvinylalcohol, polyvinylpyrrolidone, sodium carboxymethyl cellulose, carbopol, sodium alginate, xanthan gum, locust bean gum, cellulose gum, gellan gum, tragacanth gum, karaya gum, guar gum, acacia gum, psyllium and a mixture thereof.

8. The pharmaceutical composition of claim 4, wherein the amount of the hydrophilic hydrogel is in the range of 10 to 1,000 parts by weight, based on 100 parts by weight of the lipase inhibitor.

9. The pharmaceutical composition of claim 1, wherein the pharmaceutically acceptable additive is selected from the group consisting of binders, diluents, swelling agents, surfactants, lubricants, antioxidants, effervescent agents, flavors and a mixture thereof.

10. The pharmaceutical composition of claim 9, wherein the binder is selected from the group consisting of polyvinylpyrrolidone, kopovidone, gelatin, starch, sucrose, methyl cellulose, ethyl cellulose, hydroxyethyl cellulose, hydroxypropyl cellulose, hydroxypropyl alkyl cellulose and a mixture thereof.

11. The pharmaceutical composition of claim 9, wherein the diluent is selected from the group consisting of lactose, dextrin, mannitol, sorbitol, starch, microcrystalline cellulose, calcium hydrogen phosphate, anhydrous calcium hydrogen phosphate, calcium carbonate, sugars and a mixture thereof.

12. The pharmaceutical composition of claim 9, wherein the swelling agent is selected from the group consisting of cross-linked polyvinylpyrrolidone, cross-linked sodium carboxymethyl cellulose, cross-linked calcium carboxymethyl cellulose, cross-linked carboxymethyl cellulose, sodium starch glycolate, carboxymethyl starch, sodium carboxymethyl starch, potassium methacrylate-divinylbenzene copolymer, amylose, cross-linked amylose, starch derivatives, microcrystalline cellulose and cellulose derivatives, cyclodextrin and dextrin derivatives, and a mixture thereof.

13. The pharmaceutical composition of claim 9, wherein the surfactant is selected from the group consisting of poly (oxyethylene) sorbitan fatty acid ester, poly(oxyethylene) stearate, poly(oxyethylene) alkyl ether, polyglycolated glyceride, poly(oxyethylene) caster oil, sorbitan fatty acid ester, poloxamer, fatty acid salt, bile salt, alkyl sulfate, lecithin, mixed micelle of bile salt and lecithin, glucose ester vitamin E TPGS, sodium lauryl sulfate and a mixture thereof.

14. The pharmaceutical composition of claim 9, wherein the lubricant is selected from the group consisting of stearic acid, stearic acid salt, talc, corn starch, carnauba wax, light anhydrous silicic acid, magnesium silicate, synthetic aluminum silicate, hardened oil, white beeswax, titanium oxide, microcrystalline cellulose, Macrogol 4000 and 6000, isopropyl myristate and calcium hydrogen phosphate.

15. A method for preparing an oral formulation of a lipase inhibitor, which comprises
1) mixing a lipase inhibitor and a pharmaceutically acceptable additive to obtain a mixture, and optionally granulating the resulting mixture to obtain granules;
2) mixing a lipophilic oil absorbent hydrogenated castor oil, hydrogenated vegetable oil, and a pharmaceutically acceptable additive, and granulating the resulting mixture to obtain granules;
3) coating the granules obtained in 2) with an enteric coating agent; and
4) formulating the coated granules obtained in 3) and the mixture or granules obtained in 1), separately, and mixing the resulting formulations; or mixing the coated granules obtained in 3) and the mixture or granules obtained in 1), followed by formulating the resulting mixture.

16. The method of claim 15, wherein a hydrophilic hydrogel, an anti-flatulent agent or a mixture thereof is further added in step 1) or 2).

17. The method of claim 15, wherein the enteric coating agent is selected from the group consisting of ethyl cellulose, shellac, ammonio methacrylate copolymer, aminoalkyl methacrylate copolymer, methacrylic acid copolymer, polyvinylacetate, polyvinylpyrrolidone, polyvinylalcohol, hydroxymethyl cellulose, hydroxyethyl cellulose, hydroxypropyl cellulose, hydroxybutyl cellulose, hydroxypentyl cellulose, hydroxypropyl methyl cellulose, hydroxypropyl butyl cellulose, hydroxypropyl pentyl cellulose, hydroxyalkyl cellulose phthalate, sodium cellulose acetate phthalate, cellulose acetyl phthalate, cellulose ether phthalate, an anionic copolymer of methacylic acid and methyl or ethyl methacrylate, hydroxypropyl methyl cellulose phthalate, hydroxypropyl methyl cellulose acetate succinate, cellulose acetyl phthalate, and a mixture thereof.

18. An oral formulation of a lipase inhibitor prepared by the method of claim 15.

19. The oral formulation of claim 18, wherein the formulation is in the form of a tablet, chewable tablet, coated tablet, pill, powder, capsule, sachet, syrup, emulsion, microemulsion or suspension.

* * * * *